(12) United States Patent
Minai et al.

(10) Patent No.: US 8,430,818 B2
(45) Date of Patent: Apr. 30, 2013

(54) CAPSULE MEDICAL APPARATUS

(75) Inventors: Tetsuo Minai, Hachioji (JP); Kazuaki Tamura, Hachioji (JP); Jin Ohara, Hachioji (JP)

(73) Assignee: Olympus Corporation, Tokyo (JP)

( * ) Notice: Subject to any disclaimer, the term of this patent is extended or adjusted under 35 U.S.C. 154(b) by 1375 days.

(21) Appl. No.: 11/977,680

(22) Filed: Oct. 25, 2007

(65) Prior Publication Data

US 2008/0103356 A1    May 1, 2008

(30) Foreign Application Priority Data

Nov. 1, 2006   (JP) ................................ 2006-298092

(51) Int. Cl.
*A61B 5/02* (2006.01)

(52) U.S. Cl.
USPC .......................................... 600/302; 600/343

(58) Field of Classification Search ................... 600/302, 600/309, 343
See application file for complete search history.

(56) References Cited

U.S. PATENT DOCUMENTS

| | | | | | |
|---|---|---|---|---|---|
| 3,719,183 | A | * | 3/1973 | Schwartz | 600/302 |
| 5,109,851 | A | * | 5/1992 | Jadvar et al. | 600/439 |
| 2002/0032366 | A1 | | 3/2002 | Iddan et al. | |
| 2002/0132226 | A1 | * | 9/2002 | Nair et al. | 435/4 |
| 2003/0195400 | A1 | | 10/2003 | Glukhovsky | |
| 2004/0225190 | A1 | * | 11/2004 | Kimoto et al. | 600/177 |
| 2006/0173265 | A1 | | 8/2006 | Kim et al. | |
| 2006/0243288 | A1 | | 11/2006 | Kim et al. | |

FOREIGN PATENT DOCUMENTS

| | | |
|---|---|---|
| JP | 2002-046772 A | 2/2002 |
| JP | 2002-508201 | 3/2002 |
| JP | WO 2004/056833 A1 | 8/2004 |
| JP | WO 2004/068748 A1 | 8/2004 |
| JP | 2005-095433 A | 4/2005 |
| JP | 2006-513001 | 4/2006 |
| JP | 2006-513670 | 4/2006 |
| WO | WO 99/30610 | 6/1999 |
| WO | WO 01/65995 A2 | 9/2001 |

OTHER PUBLICATIONS

Japanese Office Action, dated Feb. 7, 2012, issued in counterpart Japanese Patent Application No. 2006-298092.
Extended Supplementary European Search Report dated Apr. 8, 2011.

* cited by examiner

*Primary Examiner* — Patricia Mallari
*Assistant Examiner* — Vasuda Ramachandran
(74) *Attorney, Agent, or Firm* — Scully, Scott, Murphy & Presser, P.C.

(57) ABSTRACT

The capsule medical apparatus of the present invention is disposed in a test subject and acquires information on the inside of the test subject. The capsule medical apparatus comprises a plurality of communication electrodes that are disposed on the surface of the capsule medical apparatus and capable of communication for outputting the information acquired by the capsule medical apparatus to the outside of the test subject, a judgment section that judges whether or not the plurality of communication electrodes can perform the communication based on the state of the plurality of communication electrodes, and a control section that suspends, based on the judgment result obtained in the judgment section, the operations of at least part of various sections of the capsule medical apparatus when the plurality of communication electrodes cannot perform the communication.

6 Claims, 4 Drawing Sheets

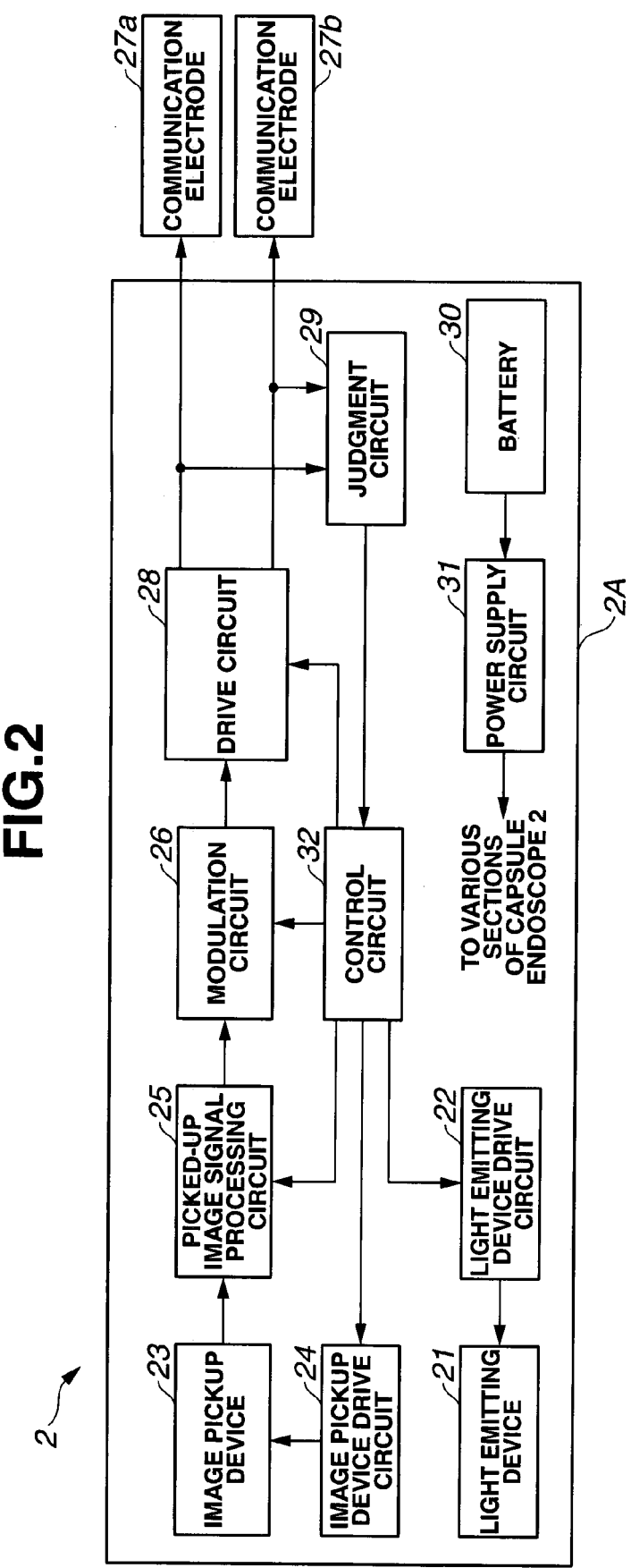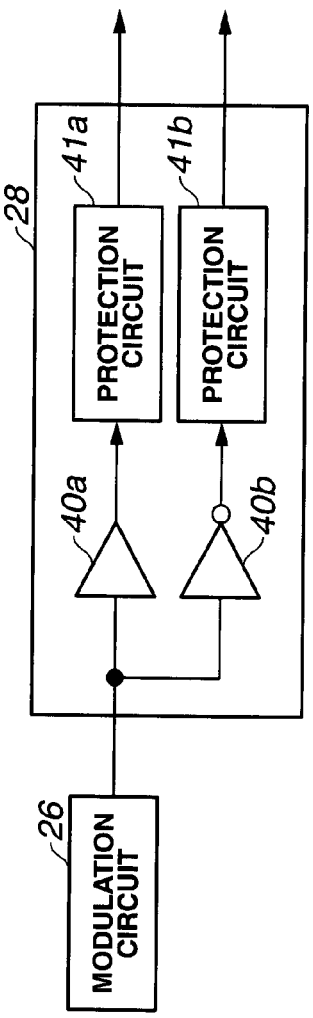

CAPSULE MEDICAL APPARATUS

CROSS REFERENCE TO RELATED APPLICATION

This application claims benefit of Japanese Application No. 2006-298092 filed on Nov. 1, 2006, the contents of which are incorporated by this reference.

BACKGROUND OF THE INVENTION

1. Field of the Invention

The present invention relates to a capsule medical apparatus, and particularly to a capsule medical apparatus that is disposed in a test subject and acquires information on the inside of the test subject.

2. Description of the Related Art

Endoscopes have been widely used in a medical field and the like. In particular, endoscopes in a medical field are primarily used to observe the inside of living organisms. One type of the endoscopes described above that has been proposed in recent years is a capsule endoscope that is swallowed by a test subject so that the capsule endoscope is disposed in a body cavity, the capsule endoscope capable of picking up images of subjects while moving along the body cavity through peristaltic movement, and sending the picked-up images of the subjects to the outside as a picked-up image signal.

An exemplary apparatus having the substantially same function as that of the capsule endoscope described above is an in-vivo image pickup apparatus described in Published Japanese translation of PCT international application No. 2003-526268.

Published Japanese translation of PCT international application No. 2003-526268 discloses the configuration of the apparatus with a built-in switch capable of on/off switching of a power supply for various sections of the apparatus using a magnetic field supplied from the outside of the apparatus. Specifically, the apparatus disclosed in Published Japanese translation of PCT international application No. 2003-526268 has a configuration in which, for example, when the apparatus is stored (not used) in a package with a magnet, the switch is turned off, and the switch is not turned on until the apparatus is removed (used) from the package with a magnet.

However, the apparatus disclosed in Published Japanese translation of PCT international application No. 2003-526268 has a problem of a large size of the apparatus body because the apparatus has the switch capable of on/off switching of various sections of the apparatus using a magnetic field supplied from the outside of the apparatus, as described above.

Furthermore, to efficiently perform the capsule endoscope function of picking up images of subjects while moving along the body cavity through peristaltic movement, and sending the picked-up images of the subjects to the outside as a picked-up image signal, the apparatus also needs to be configured in such a way that power consumption of the capsule endoscope can be reduced when the capsule endoscope is not used.

The present invention has been made in view of the above respects and aims to provide a capsule medical apparatus that can be reduced in size and can reduce power consumption when the apparatus is not used.

SUMMARY OF THE INVENTION

The capsule medical apparatus in the present invention is disposed in a test subject and acquires information on the inside of the test subject. The capsule medical apparatus comprises a plurality of communication electrodes that are disposed on the surface of the capsule medical apparatus and capable of communication for outputting the information acquired by the capsule medical apparatus to the outside of the test subject, a judgment section that judges whether or not the plurality of communication electrodes can perform the communication based on the state of the plurality of communication electrodes, and a control section that suspends, based on the judgment result obtained in the judgment section, the operations of at least part of various sections of the capsule medical apparatus when the plurality of communication electrodes cannot perform the communication.

In a preferred embodiment of the capsule medical apparatus in the present invention, the judgment section judges, based on the state of the plurality of communication electrodes, that the plurality of communication electrodes can perform the communication when the plurality of communication electrodes are closed, while judging that the plurality of communication electrodes cannot perform the communication when the plurality of communication electrodes are open.

In a preferred embodiment of the capsule medical apparatus in the present invention, the judgment section judges whether the plurality of communication electrodes are open or closed based on the impedance or the voltage value difference between the plurality of communication electrodes.

In a preferred embodiment of the capsule medical apparatus in the present invention, the capsule medical apparatus is stored with the plurality of communication electrodes open.

A preferred embodiment of capsule medical apparatus in the present invention further comprises an illumination section that illuminates a subject present in the test subject and an image pickup section that picks up an image of the subject illuminated by the illumination section. The control section suspends, based on the judgment result obtained in the judgment section, the operations of at least the illumination section and the image pickup section among various sections of the capsule medical apparatus when the plurality of communication electrodes cannot perform the communication.

BRIEF DESCRIPTION OF THE DRAWINGS

FIG. 2 is a block diagram showing an example of the internal configuration of the capsule medical apparatus in FIG. 1;

FIG. 3 shows an example of the detailed configuration of a drive circuit in FIG. 2;

DETAILED DESCRIPTION OF THE PREFERRED EMBODIMENTS

An embodiment of the present invention will be described below with reference to the drawings.

Figure 1:
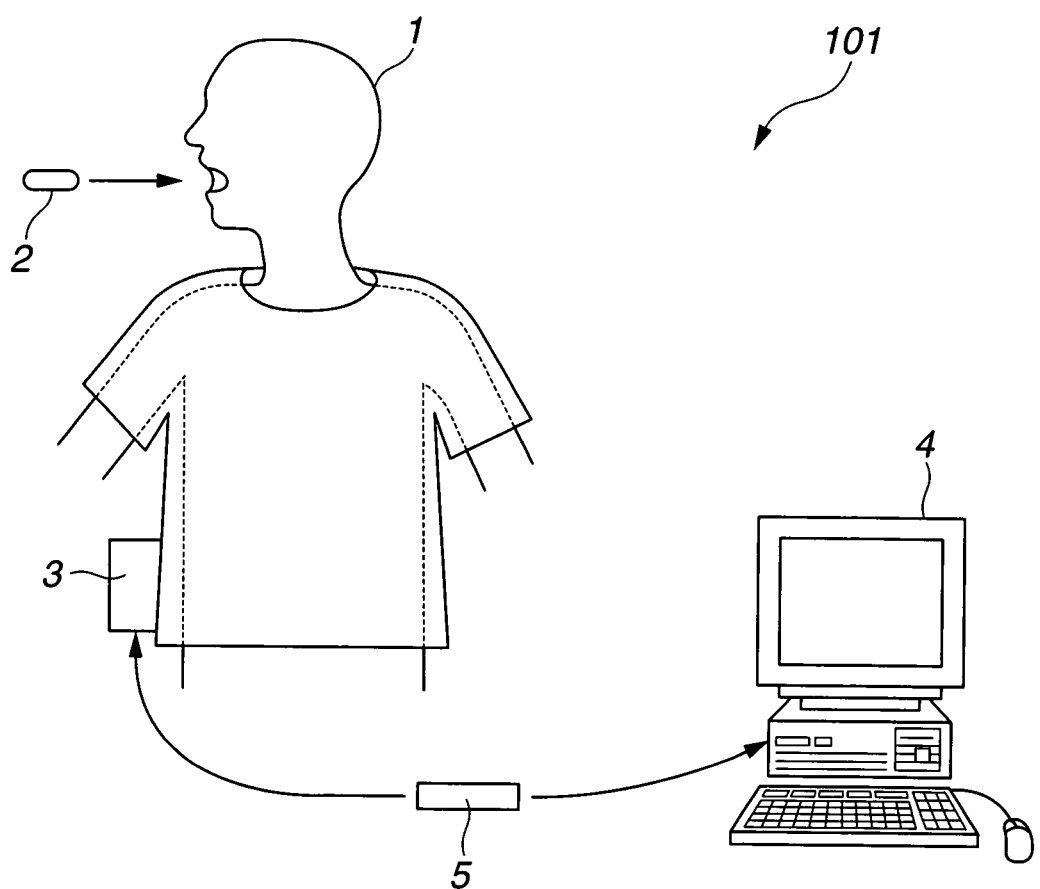
FIG. 1 shows an example of the configuration of the main portion of a test subject information acquisition system using a capsule medical apparatus of the present embodiment.

FIGS. 1 to 5 relate to the embodiment of the present invention. FIG. 1 shows an example of the configuration of the main portion of a test subject information acquisition system using a capsule medical apparatus of the present embodiment. FIG. 2 is a block diagram showing an example of the internal configuration of the capsule medical apparatus in FIG. 1. FIG.

Figure 4:
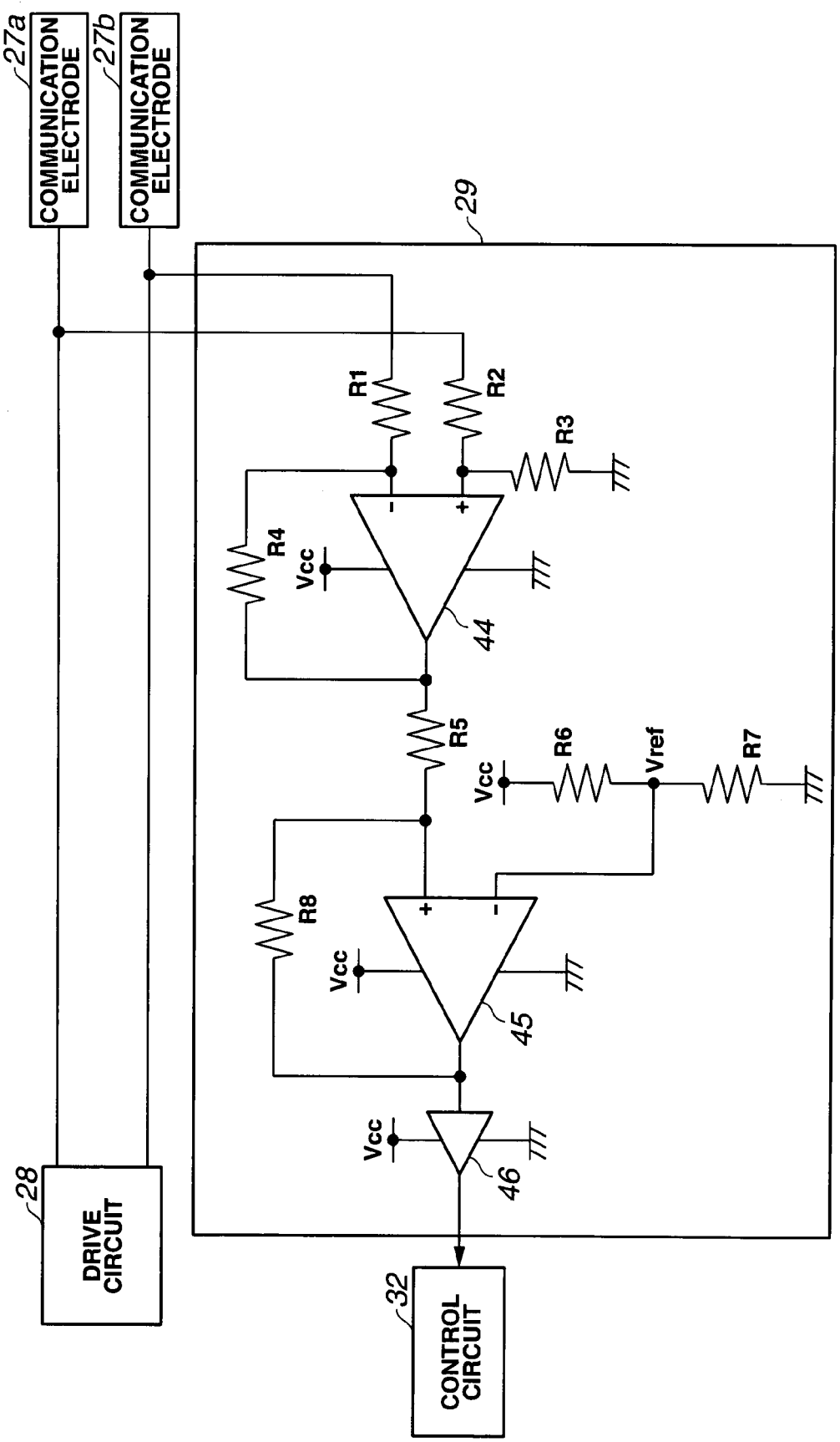
FIG. 4 shows an example of the detailed configuration of a judgment circuit in FIG. 2.
Figure 5:
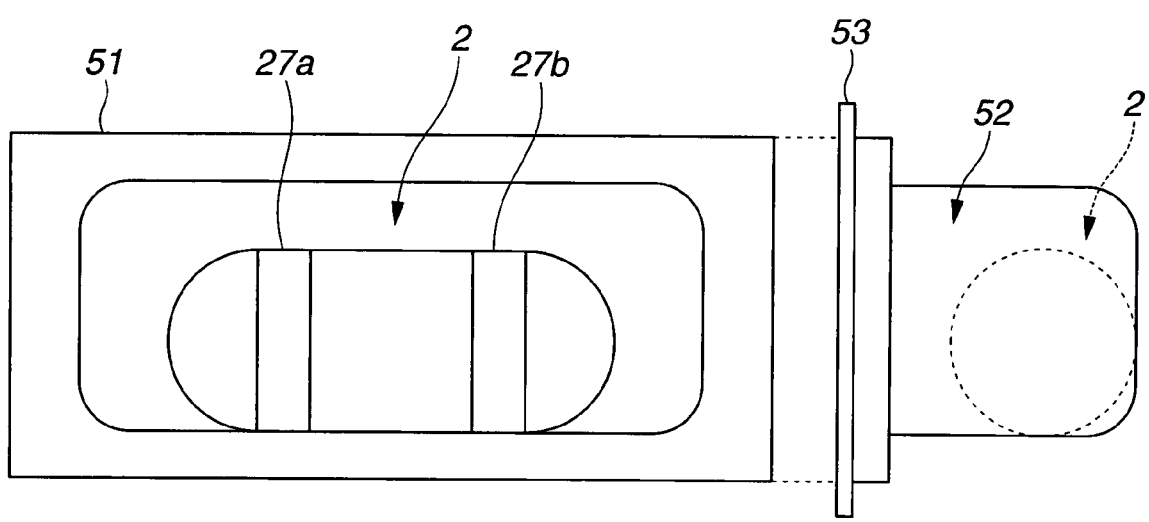
FIG. 5 shows an example of the unused state of the capsule medical apparatus in FIG. 1.

3 shows an example of the detailed configuration of a drive circuit in FIG. 2. FIG. 4 shows an example of the detailed configuration of a judgment circuit in FIG. 2. FIG. 5 shows an example of the unused state of the capsule medical apparatus in FIG. 1.

A test subject information acquisition system 101 includes, as shown in FIG. 1, a capsule medical apparatus 2 swallowed by a test subject 1 so that the capsule medical apparatus 2 is disposed in a body cavity, the capsule medical apparatus 2 picking up an image of a subject present in the body cavity, a communication apparatus 3 disposed on the outer surface of the test subject 1 and capable of communicating with the capsule medical apparatus 2, a terminal apparatus 4 that performs processes based on a signal or the like received by the communication apparatus 3 and displays the image of the subject, and a mobile storage medium 5 capable of inputting, outputting and recording data and the like stored in the communication apparatus 3 and the terminal apparatus 4. These apparatuses form the main portion of the test subject information acquisition system 101.

The capsule medical apparatus 2 includes, as shown in FIG. 2, a light emitting device 21 that is formed of, for example, an LED and emits illumination light for illuminating a subject in the test subject, a light emitting device drive circuit 22 that controls the state of the driven light emitting device 21, an image pickup device 23 formed of, for example, a CCD (Charge Coupled Device), the image pickup device 23 picking up an image of the subject illuminated by the light emitting device 21 and outputting the image of the subject as a picked-up image signal, an image pickup device drive circuit 24 that controls the state of the driven image pickup device 23, a picked-up image signal processing circuit 25 that performs signal processing on the picked-up image signal outputted from the image pickup device 23, a modulation circuit 26 that modulates the picked-up image signal on which the picked-up image signal processing circuit 25 has performed the signal processing, and communication electrodes 27a and 27b disposed on the surface of a housing 2A of the capsule medical apparatus 2. The illumination section in the present embodiment includes the light emitting device 21 and the light emitting device drive circuit 22. The image pickup section in the present embodiment includes the image pickup device 23 and the image pickup device drive circuit 24.

The capsule medical apparatus 2 further includes a drive circuit 28 that drives the communication electrodes 27a and 27b based on the picked-up image signal outputted from the modulation circuit 26, a judgment circuit 29 that judges whether the communication electrodes 27a and 27b are in the open (high impedance) state or the closed (low impedance or short-circuit) state, a battery 30, a power supply circuit 31 that generates a power supply voltage Vcc for operating the various sections of the capsule medical apparatus 2 based on the power stored in the battery 30, and a control circuit 32 that primarily controls the operations of the light emitting device drive circuit 22, the image pickup device drive circuit 24, the picked-up image signal processing circuit 25, the modulation circuit 26, and the drive circuit 28.

The housing 2A of the capsule medical apparatus 2 is harmless to living organisms and made of an insulating material, such as resin, which does not conduct electricity from the outside.

The communication electrodes 27a and 27b have corrosion resistance to digestive juice and the like and are made of a conductive material, such as SUS316L or gold, which is harmless to living organisms. When the drive circuit 28 drives the communication electrodes 27a and 27b, an electric current flows from one of the electrodes having a higher voltage value to the other electrode having a lower voltage value through the surface of the test subject 1. In this way, the electric signal according to the picked-up image signal outputted from the image pickup device 23 can be outputted to the communication apparatus 3 disposed on the outer surface of the test subject 1.

The drive circuit 28 includes, as shown in FIG. 3, buffers 40a and 40b that generate electrode drive signals for driving the communication electrodes 27a and 27b based on the picked-up image signal modulated in the modulation circuit 26 and output the generated electrode drive signals, and protection circuits 41a and 41b for protecting the buffers 40a and 40b.

In such a configuration, the electrode drive signal generated based on the picked-up image signal inputted to the buffer 40a is outputted to the protection circuit 41a with the phase unchanged with respect to the picked-up image signal. On the other hand, in the configuration described above, the electrode drive signal generated based on the picked-up image signal inputted to the buffer 40b is outputted to the protection circuit 41b with the phase shifted by 180 degrees with respect to the picked-up image signal.

Each of the protection circuits 41a and 41b includes a resister having, for example, approximately a few hundred ohms, and/or a capacitor to protect the buffers 40a and 40b even if the communication electrodes 27a and 27b are short-circuited.

The judgment circuit 29 as a judgment section includes, as shown in FIG. 4, a differential amplifier 44 that detects the voltage value difference between the electrode drive signals outputted from the drive circuit 28 and outputs a voltage difference signal according to the resistance values of resistors R1, R2, R3 and R4, a comparator 45 that compares the voltage value of the voltage difference signal outputted from the differential amplifier 44 with the value of a comparison voltage Vref (Vref<Vcc) determined according to the resistance values of resistors R6 and R7 and outputs a comparison result signal having the voltage value according to the comparison result and the resistance values of resistors R5 and R8, and a buffer 46 that converts the comparison result signal outputted from the comparator 45 into a logical value (value "0" or "1") that the control circuit 32 can receive and outputs the logical value.

That is, the judgment circuit 29 judges whether or not the communication electrodes 27a and 27b are open by generating the voltage difference signal, using the differential amplifier 44, according to the voltage value difference between the electrode drive signals outputted from the drive circuit 28, outputting the generated voltage difference signal, and using the comparator 45 to detect whether or not the voltage value of the voltage difference signal is greater than the comparison voltage value Vref. In this way, when the voltage value of the voltage difference signal outputted from the differential amplifier 44 is greater than the comparison voltage value Vref, the judgment circuit 29 judges that the communication electrodes 27a and 27b are open, so that the communication electrodes 27a and 27b cannot perform communication. On the other hand, when the voltage value of the voltage difference signal outputted from the differential amplifier 44 is smaller than or equal to the comparison voltage value Vref, the judgment circuit 29 judges that the communication electrodes 27a and 27b are closed, so that the communication electrodes 27a and 27b can perform communication.

The differential amplifier 44 and the comparator 45 are not limited to those formed of analog devices, but may be those formed of digital devices as long as they have similar functions.

The operation of the test subject information acquisition system 101 using the capsule medical apparatus 2 of the present embodiment will now be described.

The capsule medical apparatus 2, when not used, is stored in a storage recess well 52 in a package 51 with a lid 53 closed, for example, as shown in FIG. 5.

The package 51 is made of, for example, a water-resistant or water repellent, insulating material and configured to keep water-tightness when the lid 53 is closed. Since the package 51 has the configuration described above, the capsule medical apparatus 2, when not used, is stored in such a way that the capsule medical apparatus 2 is insulated and does not directly come into contact with liquid. The capsule medical apparatus 2 may be stored and supported by, for example, a shock-absorbing material or a supporting material in such a way that the capsule medical apparatus 2 will not move in the package 51 or the capsule medical apparatus 2 will not directly receive external pressure. In this case, the shock-absorbing material or the supporting material may preferably be made of an insulating material.

On the other hand, the communication electrodes 27a and 27b are open when the capsule medical apparatus 2 is stored in the package 51. When the judgment circuit 29 judges that the communication electrodes 27a and 27b are open (the communication electrodes 27a and 27b cannot perform communication), the control circuit 32 follows the judgment result and suspends the operations of the light emitting device drive circuit 22, the image pickup device drive circuit 24, the picked-up image signal processing circuit 25, and the modulation circuit 26. This also suspends the operations of the light emitting device 21 and the image pickup device 23 as well as those of the sections described above. The modulation circuit 26 keeps outputting a signal at a GND level during the operation suspended period.

The drive circuit 28 outputs a signal having a voltage value at the GND level as the electrode drive signal via the buffer 40a and the protection circuit 41a when the operation of the modulation circuit 26 is suspended. The drive circuit 28 also outputs a signal having a voltage value of the power supply voltage Vcc as the electrode drive signal via the buffer 40b and the protection circuit 41b when the operation of the modulation circuit 26 is suspended.

When the differential amplifier 44 and the comparator 45 detect that the voltage value difference between the electrode drive signals is greater than the comparison voltage value Vref, the judgment circuit 29 outputs the judgment result that the communication electrodes 27a and 27b are open to the control circuit 32 via the buffer 46. When the judgment circuit 29 is outputting the judgment result that the communication electrodes 27a and 27b are open, the control circuit 32 as the control section keeps controlling the operations of the light emitting device drive circuit 22, the image pickup device drive circuit 24, the picked-up image signal processing circuit 25, and the modulation circuit 26 to be suspended. At this point, the light emitting device 21, which is the component of the illumination section of the present embodiment, and the image pickup device 23, which is the component of the image pickup section of the present embodiment, also suspend their operations. Power consumption of the capsule medical apparatus 2 not in use is thus reduced by the control circuit 32 that performs the control described above.

The capsule medical apparatus 2 is removed for use from the package 51, swallowed by the test subject 1, so that the capsule medical apparatus 2 is disposed in a body cavity.

When the capsule medical apparatus 2 is disposed in a body cavity of the test subject 1, the state of the communication electrodes 27a and 27b changes from open to closed, so that the voltage value changes from the GND level. Thus, the voltage value difference between the electrode drive signals outputted from the drive circuit 28 decreases.

When the differential amplifier 44 and the comparator 45 detect that the voltage value difference between the electrode drive signals is smaller than or equal to the comparison voltage value Vref, the judgment circuit 29 outputs the judgment result that the communication electrodes 27a and 27b are closed to the control circuit 32 via the buffer 46. When the judgment circuit 29 judges that the communication electrodes 27a and 27b are closed (the communication electrodes 27a and 27b can perform communication), the control circuit 32 follows the judgment result and controls the light emitting device drive circuit 22, the image pickup device drive circuit 24, the picked-up image signal processing circuit 25, and the modulation circuit 26 to be operated. This also initiates the operations of the light emitting device 21 and the image pickup device 23 as well as those of the sections described above.

As described above, the capsule medical apparatus 2 of the present embodiment has a configuration without a dedicated switch and the like to change the state of the apparatus into operation. As a result, the capsule medical apparatus 2 of the present embodiment has a more compact configuration than that conventionally achievable and can reduce power consumption when not used.

The capsule medical apparatus 2 of the present embodiment is not limited to the one that communicates with the communication apparatus 3 disposed on the outer surface of the test subject 1 by conducting an electric current on the surface of the test subject 1, but may be the one that communicates with the communication apparatus 3 by inducing an electric field or a magnetic field oriented to the surface of the test subject 1.

The present invention is not limited to the above embodiment, but various changes and applications are of course possible to the extent that they do not depart from the spirit of the present invention.

What is claimed is:

1. A capsule medical apparatus comprising:
   an encapsulated body adapted to be disposed within a test subject;
   an information acquisition section arranged to the encapsulated body, the information acquisition section being configured to perform at least one function to acquire information;
   a plurality of communication electrodes arranged on an external surface of the encapsulated body and adapted to be in contact with the test subject in which the encapsulated body is disposed, the plurality of communication electrodes being capable, based on the characteristic of the test subject that the plurality of communication electrodes are in contact with, of communicating the acquired information to the outside of the encapsulated body;
   a judgment section configured to judge whether or not the plurality of communication electrodes are capable, based on the characteristic of the test subject that the plurality of communication electrodes are in contact with, of communicating the acquired information to the outside of the encapsulated body; and
   a control section configured to control the information acquisition section to suspend, based on the judgment result obtained in the judgment section, the performance of one or more of the at least one function of the information acquisition section when the plurality of communication electrodes are not capable, based on the characteristic of the test subject that the plurality of communication electrodes are in contact with, of communicating the acquired information to the outside of the encapsulated body.

2. The capsule medical apparatus according to claim 1, wherein the judgment section is configured to judge, based on the state of the plurality of communication electrodes, that the plurality of communication electrodes can perform the communication when the plurality of communication electrodes are closed, and that the plurality of communication electrodes cannot perform the communication when the plurality of communication electrodes are open.

3. The capsule medical apparatus according to claim 2, wherein the judgment section is configured to judge whether the plurality of communication electrodes are open or closed based on the impedance or the voltage value difference between the plurality of communication electrodes.

4. The capsule medical apparatus according to claim 2, wherein the capsule medical apparatus is stored with the plurality of communication electrodes open.

5. The capsule medical apparatus according to claim 3, wherein the capsule medical apparatus is stored with the plurality of communication electrodes open.

6. The capsule medical apparatus according to claim 3, wherein:
  the information acquisition section includes:
    an illumination section configured to illuminate a subject present in the test subject in which the encapsulated body is disposed, and
    an image pickup section configured to pick up an image of the subject illuminated by the illumination section, and
  the control section is configured to suspend, based on the judgment result obtained in the judgment section, the operations of the illumination section and the image pickup section when the plurality of communication electrodes are not capable, based on the characteristic of the test subject that the plurality of communication electrodes are in contact with, of communicating the acquired information to the outside of the encapsulated body.

* * * * *